US006982271B1

(12) United States Patent
Kozikowski et al.

(10) Patent No.: US 6,982,271 B1
(45) Date of Patent: Jan. 3, 2006

(54) TROPANE ANALOGS

(75) Inventors: Alan P. Kozikowski, Princeton, NJ (US); Wolfgang Alexander Hoepping, Dresden (DE)

(73) Assignee: Georgetown University, Washington, DC (US)

( * ) Notice: Subject to any disclaimer, the term of this patent is extended or adjusted under 35 U.S.C. 154(b) by 41 days.

(21) Appl. No.: 09/671,104

(22) Filed: Sep. 27, 2000

Related U.S. Application Data

(60) Provisional application No. 60/156,275, filed on Sep. 27, 1999.

(51) Int. Cl.
*A61K 31/46* (2006.01)
*C07D 471/18* (2006.01)
*A61P 25/00* (2006.01)

(52) U.S. Cl. .................... 514/295; 514/304; 546/97; 546/124; 546/125

(58) Field of Classification Search ............... 514/295, 514/304; 546/97, 124, 125
See application file for complete search history.

(56) References Cited

U.S. PATENT DOCUMENTS 6,150,376 A * 11/2000 Kozikowski et al. ....... 514/299

FOREIGN PATENT DOCUMENTS

WO    WO 92/01688    2/1992
WO    WO 97/16451    5/1997

OTHER PUBLICATIONS

Hoepping et al.; "Novel Conformationally Constrained Tropane Analogues by 6–endo–trig Radical Cyclization and Stille Coupling—Switch of Activity Toward the Serotonin and/or Norepinephrine Transporter", J. Med. Chem. 43: 2064–2071, (2000).
Corey et al.; "A Stereoselective Synthesis of (±)–11–Hydroxy–trans–8–dodecenoic Acid Lactone, a Naturally Occuring Macrolide From Cephalosporium Recifei", Journal of the American Chemical Society 98(1): 222–224, (Jan. 7, 1976).
Stille and Groh; "Stereospecific Cross–Coupling of Vinyl Halides with Vinyl Tin Reagents Catalyzed by Palladium", J. Am. Chem. Soc. 109: 813–817, (1987).
Nozaki et al.; "Et $_3$ B–Induced Radical Addition of R$_3$ SnH to Acetylenes and Its Application to Cyclization Reaction", J. Am. Chem. Soc. 109: 2547–2549, (1987).
Smith et al.; "Tuning the Selectivity of Monoamine Transporter Inhibitors by the Stereochemistry of the Nitrogen Lone Pair", J. Am. Chem. Soc. 120: 9072–9073, (1998).

Kilty et al.; "Cloning and Expression of Cocaine–Sensitive Rat Dopamine Transporter", Science, 254:578–579, (Oct. 25, 1991).
Nelson Nathan; "The Family of Na $^+$/C1—Neurotransmitter Transporters", Journal of Neurochemistry71: 1785–1803, (1998).
Byrne and Rothschild; "Loss of Antidepressant Efficacy During Maintenance Therapy: Possible Mechanisms and Treatments", J. Clin. Psychiatry, 59(6): 279–288, (Jun. 1998).
Caroll et al.; "Synthesis, Ligand Binding, and QSAR (CoMFA and Classical) Atudy of 3β–(3' –Substituted Phenyl)–, and 3β–(3', 4' –Disubstituted Phenyl)tropane–2β–Carboxylic Acid Methyl Esters", J. Med. Chem. 37: 2865–2873, (1994).
Owens et al.; "Neurotranmitter Receptor and Transporter Binding Profile of Antidepressants and Their Metabolites", The Journal of Pharmacology and Experimental Therapeutics, 283(3): 1305–1322, (1997).
Olofson et al.; "A New Reagent for the Selective, High–Yeild N– Dealkylation of Tertiary Amines: Improved Syntheses of Naltrexone and Nalbuphine", The Journal of Organic Chemistry 49:2081–2082, (1984).
Lapin and Oxenkurg, Intensification of the Central Seretoninergic Processes as a Possible Determinant of the Thymoleptic Effect, The Lancet, 1: 132–136 (Jan. 18, 1969).
Horst and Preskorn, "Mechanisms of Action and Clinical Characterisitics of Three Atypical Antidepressants: Venlafaxine, Nefazodone, Bupropion", Journal of Affective Disorders 51: 237–254, (1998).
Schildkraut and J. Joseph; "The Catecholamine Hypothesis of Affective Disorders: A Review of Supporting Evidence", The American Journal of Psychiatry, 122: 509–522, (1965).
Boyd and Weissman; "Epidemiology of Affective Disorders", Arch. Gen. Psychiatry, 38:1039–1046 (Sep. 1981).
Broekkamp et al.; "Prospects for Improved Antidepressants", Journal of Medicinal Chemistry, 38(23): 4615–4633, (Nov. 10, 1995).
International Search Report, mailed on Jul. 27, 2001.

* cited by examiner

*Primary Examiner*—Evelyn Mei Huang
(74) *Attorney, Agent, or Firm*—Dana M. Gordon; Foley Hoag LLP (57) ABSTRACT

The present invention provides compounds, specifically novel tropane analogs, capable of acting as inhibitors of reuptake of monoamines. In preferred embodiments, these compositions are selective inhibitors of serotonin and/or norepinephrine reuptake. Also provided herein are pharmaceutical compositions comprising novel tropane analogs and a pharmaceutically acceptable carrier, and methods for treating conditions in which inhibition of reuptake of monoamines is desired. The inventive compositions as described herein are also useful for medical therapy and diagnosis.

16 Claims, 3 Drawing Sheets

Reagents and conditions: (a) CH$_3$CHClOCOCl; 1,2-DCE; K$_2$CO$_3$; MeOH; 92% (b) propargyl bromide; K$_2$CO$_3$; MeCN; 84% (c) 1N HCl; POCl$_3$; MeOH; -78 C --> rt; 82% (d) AIBN; $n$-Bu$_3$SnH; PhH; 73% (e) RI; CuI; (o-Tol)$_3$P; Pd$_2$(dba)$_3$; DMF; 8-65%.

*FIGURE 3*

TROPANE ANALOGS

RELATED APPLICATIONS

This application claims the benefit under 35 USC §119(e) of the filing date of U.S. Provisional Pat. Application Ser No. 60/156,275, filed September 27, 1999.

This invention was made with government support under grant number R01 DA010458 awarded by the National Institutes of Health. The Government has certain rights in the invention.

BACKGROUND OF THE INVENTION

Clinical depression is a neurological disorder that affects a steadily increasing number of the population. Currently, two generations of antidepressants are utilized by physicians. The discovery of the tricyclic antidepressants (TCA) and the monoamine oxidase inhibitors were the first generation of antidepressants. Although these represented a radical approach to the therapy of depression, TCA and monoamine oxidase inhibitors suffer from serious side effects and toxicity in overdose. As a result, a second generation of antidepressants with an improved safety profile were developed, for example, the selective serotonin reuptake inhibitors (SSRI), reversible monoamine oxidase inhibitors, and other compounds with different mechanisms of action, like bupropion, nefazodone and venlafaxine. These antidepressants are largely devoid of anticholinergic and cardiovascular side effects. However, they do not exhibit a broader efficacy over TCAs, and SSRIs are less effective in severe forms of depression and lose efficacy over time. A further disadvantage of nearly all currently used antidepressants is their slow onset of action. In general, antidepressants require several weeks (2–6 weeks) of continuous administration before their mood elevating properties become manifest. Currently, no antidepressants with an efficacy >70% and a fast onset of action (<2–3 weeks) are available.

The monoamine theory of depression still remains the prevailing basis for the design of safer and more potent antidepressants. This theory postulates that the illness arises as a consequence of a defect in the synaptic availability of monoamines, particularly serotonin and norepinephrine. While not wishing to be bound to any particular theory, it is believed that administration of antidepressants blocks uptake of such monoamines and increases the amount of neurotransmitters in the synaptic cleft and therefore enhances their availability at pre- and postsynaptic receptors. However, mood-elevating effects are usually first observed after several weeks of administration. This is probably due to adaptive changes in receptor sensitivity and density in both the serotonin and norepinephrine circuitry. Additionally, there is growing evidence that several receptors, apart from the reuptake sites, mediate antidepressive responses. Thus, it is believed that the 2, , 5-HT1A, 5-HT2A and D2 receptors contribute to the efficacy and, particularly, to a rapid onset of antidepressant action.

More generally, it is also believed that the onset of other conditions, including, but not limited to, neurodegenerative diseases (Parkinson's Disease and Alzheimer's Disease), substance addiction (e.g., cocaine addiction), Attention Deficit Disorder (ADD), and bipolar disorder, involve a defect in monoaminergic neurotransmission. Thus, the ability to block monoamine transporters (and thus block the reuptake of monoamines), and thus effect an increase in concentration of monoamines more safely and efficiently, would be useful in the treatment of any condition caused by a deficiency in monoamine concentration.

Clearly, there remains a need to develop therapeutics for the treatment of conditions caused by a deficiency in monoamine concentration, preferably for the treatment of depression, that are broadly efficacious, safe (e.g., have fewer side effects associated with them), and have a fast onset of action. Additionally, because of the role that other mechanisms and systems may play in the therapeutic response, it would be ideal to develop a class of therapeutics capable of acting at more than one target site.

SUMMARY OF THE INVENTION

In recognition of the need to develop safer and more efficacious drugs for conditions caused by a deficiency in monoamine concentration, the present invention provides compositions, specifically novel tropane analogs, capable of acting as inhibitors of reuptake of monoamines. In preferred embodiments, these compositions are selective inhibitors of serotonin and/or norepinephrine reuptake.

In one aspect, the present invention provides compositions having the formula (I):

wherein,

A is either a double bond or a single bond, n is 2 or 3, and each occurrence of $R_1$ independently comprises a moiety selected from the group consisting of hydrogen, aryl, heteroaryl, cycloalkyl, polycyclic, heterocyclic, alkenyl, alkynyl, solid support unit, polymer, and biomolecule;

$R_2$–$R_{13}$ each independently comprise a moiety selected from the group consisting of hydrogen, alkyl, alkenyl, alkynyl, aryl, heteroaryl, cycloalkyl, polycyclic, heterocyclic, alkoxy, acyl, amino, hydroxy, thio, halogen, cyano, nitro, trifluoromethyl, azido, imino, amido, phosphoryl, sulfonyl, silyl group, ether, alkylthio, carbonyl, solid support unit, polymer, and biomolecule;

$R_{14}$ comprises a functionality selected from the group consisting of ester moiety, O—$R_{15}$, wherein $R_{15}$ is selected from the group consisting of alkyl, cycloalkyl, aryl, heteroaryl, alkenyl, and alkynyl; ketone; oxime; carboxylic acid; aldehyde; phosphoryl; silyl; solid support unit; polymer and biomolecule, or a pharmaceutically acceptable salt thereof.

In particularly preferred embodiments of compositions represented by (I), preferably one occurrence of $R_1$ comprises a moiety selected from the group consisting of aryl, heteroaryl, cycloalkyl, polycyclic, heterocyclic, alkenyl, and alkynyl, and preferably, when A is a double bond and n=2, at least one occurrence of $R_1$ is hydrogen, whereby either an E (entgegen) or Z (zusammen) isomer is formed; $R_2$–$R_{13}$ each independently comprise hydrogen or alkyl; and $R_{14}$ comprises an ester moiety.

In still other preferred embodiments of compositions represented by (I), when n=2 or 3, preferably one occurrence of $R_1$ comprises a moiety selected from the group consisting of haloaryl, alkoxy, alkylaryl, polycyclyl, alkenylaryl, and alkynylaryl and is most preferably selected from the group consisting of phenyl, 3,4-Dichloro-phenyl, 4-methoxy-phenyl, 4-fluoro-phenyl, 1-napthyl, 2-furyl, and 3-furyl, methoxy, and substituted or unsubstituted alkenylaryl; and either one or two occurrences of $R_1$ comprise hydrogen.

In particularly preferred embodiments of compositions represented by (I), A is a double bond, n=2, and one occurrence of $R_1$ is selected from the group consisting of phenyl, 3,4-Dichloro-phenyl, 4-methoxy-phenyl, 4-fluoro-phenyl, 1-napthyl, 2-furyl, 3-furyl, methoxy, and substituted or unsubstituted alkenylaryl, and the second occurrence of $R_1$ is hydrogen, whereby an E (entgegen) isomer is generated.

The present invention also preferably provides compositions having the formula (II):

(II)

wherein, $R_1$ and $R_2$ each independently comprise a moiety selected from the group consisting of hydrogen, aryl, heteroaryl, cycloalkyl, polycyclic, heterocyclic, alkenyl, alkynyl, solid support unit, polymer, and biomolecule;

$R_3$–$R_{13}$ each independently comprise a moiety selected from the group consisting of hydrogen, alkyl, alkenyl, alkynyl, aryl, heteroaryl, cycloalkyl, polycyclic, heterocyclic, alkoxy, acyl, amino, hydroxy, thio, halogen, cyano, nitro, trifluoromethyl, azido, imino, amido, phosphoryl, sulfonyl, silyl group, ether, alkylthio, carbonyl, solid support unit, polymer, and biomolecule;

$R_{14}$ comprises a functionality selected from the group consisting of ester moiety, O—$R_{15}$, wherein $R_{15}$ is selected from the group consisting of alkyl, cycloalkyl, aryl, heteroaryl, alkenyl, and alkynyl; ketone; oxime; carboxylic acid; aldehyde; phosphoryl; silyl; solid support unit; polymer and biomolecule, or a pharmaceutically acceptable salt thereof.

In particularly preferred embodiments, either $R_1$ or $R_2$, but not both, comprises a moiety selected from the group consisting of aryl, heteroaryl, cycloalkyl, polycyclic, heterocyclic, alkenyl, and alkynyl, and either $R_1$ or $R_2$ comprises hydrogen, whereby either an E (entgegen) or Z (zusammen) isomer is formed; $R_3$—$R_{13}$ each independently comprise hydrogen or alkyl; and $R_{14}$ comprises an ester moiety.

In still other preferred embodiments of compositions represented by (II), either $R_1$ or $R_2$, but not both, comprises a moiety selected from the group consisting of haloaryl, alkoxy, alkylaryl, polycyclyl, alkenylaryl, and alkynylaryl and is most preferably selected from the group consisting of phenyl, 3,4-Dichloro-phenyl, 4-methoxy-phenyl, 4-fluoro-phenyl, 1-napthyl, 2-furyl, and 3-furyl, methoxy, and substituted or unsubstituted alkenylaryl, and either $R_1$ or $R_2$, but not both, comprises hydrogen.

In particularly preferred embodiments of compositions represented by (II), $R_1$ is selected from the group consisting of phenyl, 3,4-Dichloro-phenyl, 4-methoxy-phenyl, 4-fluoro-phenyl, 1-napthyl, 2-furyl, 3-furyl, methoxy, and substituted or unsubstituted alkenylaryl, and $R_2$ is hydrogen, whereby an E (entgegen) isomer is generated.

Unexpectedly, it has been found that compounds of formula (I) and (II) are capable of binding to monoamine transporters, and inhibiting reuptake of monoamines. In certain preferred embodiments, these compounds act as potent and selective inhibitors of norepinephrine and serotonin reuptake. Certain of these compounds act either as selective norepinephrine and serotonin reuptake inhibitors (SSNRI), or act as selective norepinephrine reuptake inhibitors (SNRI).

The invention also provides pharmaceutical compositions comprising a compound of formula (I) or (II), as described herein; or a pharmaceutically acceptable salt thereof; in combination with a pharmaceutically acceptable diluent or carrier.

In general, in another aspect, the present invention relates to a method for treating a disease or condition in a mammal in which inhibition of reuptake of monoamine is desired, comprising administering a compound of formula (I) or (II); or a pharmaceutically acceptable salt thereof. The inventive compounds may thus be used for treatment of such disorders including, but not limited to depression, neurodegenerative diseases (such as Alzheimer's Disease and Parkinson's Disease), substance addiction, Attention Deficit Disorder (ADD), Huntington's Disease, bipolar disorder, and other psychiatric or clinical disfunctions. In particularly preferred embodiments, the compositions of the present invention are used to treat depression in a human.

In still another aspect, the present invention also provides a compound of formula (I) or (II); or a pharmaceutically acceptable salt thereof; for use in medical therapy or diagnosis.

In yet another aspect, the present invention provides libraries of compounds having the general formula (I) or (II), and additionally provides methods for testing these libraries of compounds for the ability to bind monoamine transporters and inhibit monoamine reuptake.

Definitions

For convenience, before further description of the invention, certain terms employed in the specification, examples, and appended claims are collected and defined below:

The term "treatment", as used herein, refers to any process, action, application, therapy, or the like, wherein an animal, including a human being, is subject to medical aid with the object of improving the animal's condition, directly or indirectly.

The term "effective dose", or "therapeutically effective dose" or "therapeutically effective amount", as used herein, means that amount of a compound, material, or composition comprising a compound of the present invention which is effective for producing some desired therapeutic effect in at least a sub-population of cells in an animal at a reasonable benefit/risk ratio applicable to any medical treatment. Doses of this composition included in the present methods and pharmaceutical compositions are preferably an efficacious, nontoxic quantity. A therapeutically effective dose can be readily determined by the attending diagnostician, as one skilled in the art, by the use of conventional techniques and by observing results obtained under analogous circumstances. In determining the therapeutically effective dose, a number of factors are considered by the attending diagnostician, including but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

The phrase, "pharmaceutically-acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem and complication, commensurate with a reasonable benefit/risk ratio.

The term "pharmaceutically-acceptable carrier", as used herein, means a pharmaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formate, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —CF3, —CN and the like. Exemplary substituted alkyls are described below. Cycloalkyls can be further substituted with alkyls, alkenyls, alkoxys, alkylthios, aminoalkyls, carbonyl-substituted alkyls, —CF3, —CN, and the like. The term "arylkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiopene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles," "heteroaryl," or "heteroaromatics". The aromatic ring can be substituted at one or more ring positions with such substituents as described above, as for example, halogen, azide, alkyl, aralkyl, alkenyl, alkeynyl, cycloalkyl, hydroxyl, amino, nitro, sulfhydryl, imino, amido, phosponate, phosphinate, carbonyl, carboxyl, silyl, ether, alkylthio, sulfonyl, solfonamido, ketone, aldehyde, ester, a heterocyclyl, an aromatic or heteroaromatic moiety, —CF3, —CN, or the like.

The terms "heterocyclyl", "heterocyclic" or "heterocyclic group" refer to 4- to 10-membered ringtructures, more preferably 4- to 7-membered rings, which ring structures include one to four heteroatoms. Heterocyclyl groups include, for example, pyrrolidine, oxolane, thiolane, imidazole, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The terms "polycyclyl", "polycyclic" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis. Furthermore, the compounds of the present invention are intended to encompass all possible geometric and stereoisomers. For example, for compounds having a double bond, the present invention is intended to encompass both E(entgegen) and Z(zusammen) isomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The term "solid support" refers to a material having a rigid or semi-rigid surface. Such materials will preferably take the form of small beads, pellets, disks, chips, dishes, multi-well plates, wafers or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "solid support unit", as used herein, refers to a unit comprising a "solid support", as defined above, and a functional moiety, such as a linker group, providing an attachment of the desired compound to the solid support unit.

The term "polymeric support", as used herein, refers to a soluble or insoluble polymer to which an amino acid or other chemical moiety can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support can be soluble under certain conditions and insoluble under other conditions.

As used herein, the term "patient" refers to a warm-blooded animal, such as a mammal, which is suffering from depression. It is understood that dogs, cats, rats, mice, horses, bovine cattle, sheep, and humans are examples of animals within the scope of the meaning of the term.

The term "depression" refers to a disease or an abnormal state or condition characterized clinically by a psychiatric syndrome comprising, for example, a dejected mood, psychomotor retardation, insomnia, weight loss, and the like. Depression is readily diagnosed by a clinical diagnostician using practices and procedures well known and appreciated by those of ordinary skill in the art.

DETAILED DESCRIPTION OF THE INVENTION

I. Overview:

As mentioned previously, the monoamine theory of depression has provided a useful model for the development of novel therapeutics for depression. Thus, based upon the previous studies of the exploration the role that inhibition of the monoamine reuptake plays in cocaine addiction, cocaine was chosen as the lead compound. Cocaine represents an ideal starting point for this purpose because of its ability to block reuptake at all three monoamine transporters. It exhibits higher activity at the serotonin transporter (5-HTT) and norepinephrine transporter (NET) in comparison to dopamine transporter (DAT). The monoamine transporters belong to a family of closely related membrane proteins containing 12 transmembrane domains. Within this group the DAT and NET are among the most closely related members, having 78% homology in their amino acid sequence. Both DAT and NET effectively transport each other's substrates.

Many of the tropane derivatives that have been prepared from cocaine with the notion of identifying a "cocaine medication" exhibit an improved activity in transporter binding and reuptake inhibition compared to cocaine itself and important progress has been made in the synthesis of more selective compounds in the inhibition of either dopamine or serotonin reuptake. For example, it has been recently shown that constraint of the nitrogen lone pair by making "front-" or "back-" bridged analogs leads to compounds with selectivity for either the 5-HTT or the DAT. Notably, NET affinity was not influenced. Relatively little is known about the role the NET might play in cocaine addiction, as there are no highly selective ligands in the tropane series that inhibit the reuptake of norepinephrine alone.

Figure 1:
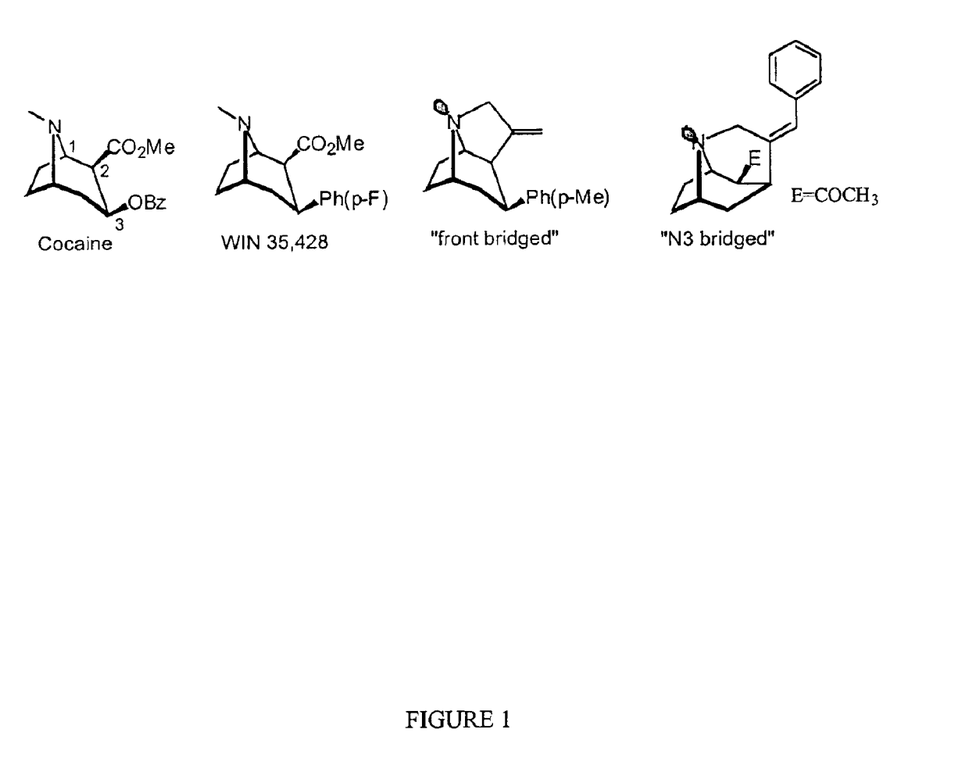
FIG. 1 depicts structures for cocaine, WIN 35,428, a "front bridged" compound and an inventive "N3 bridged" compound.

In an effort to learn more about the ability of structural analogs to inhibit reuptake of monoamine transporters, and possibly discover selective uptake inhibitors, the effect of a ring constraint between the 3-position and the nitrogen which by necessity forces the six-membered ring of the tropane moiety into a boat conformation was explored. Moreover, this modification made it possible to maintain the ester group at the 2-position, which, while not wishing to be bound to any particular theory or functional group, is believed to contribute to binding at the monoamine transporter. At the same time, the aromatic ring is displaced from its original 3-position to a position above the basal plane of the tropane ring without changing its approximate directionality. The distance between nitrogen and the centroid of the aromatic ring in the WIN compounds is about 5.63 Å. Approximately the same distance (5.64 Å) is maintained by installation of a three carbon linker between the nitrogen and the aromatic ring in the "N3 bridged" compound possessing an E-configured double bond (FIG. 1).

The ability to generate these novel "N3 bridged" compounds thus provided for the exploration of the ability of certain compositions to bind to monoamine transporters and inhibit the reuptake of monoamines. Such compositions and pharmaceutical preparations provide useful therapeutics for the treatment of conditions caused by a deficiency in monoamine concentration, including, but not limited to depression, cocaine addiction, neurodegenerative diseases (Alzheimer's Disease and Parkinson's Disease), and Attention Deficit Disorder.

II. Exemplary Compositions:

The present invention, in one aspect, provides novel tropane analogs capable of binding to monoamine transporters and acting as inhibitors of reuptake of monoamine neurotransmitters, preferably as selective inhibitors of serotonin and norepinephrine reuptake. In one embodiment, the compositions of the present invention are generally represented by formula (I) below:

(I)

wherein,
A is either a double bond or a single bond, n is 2 or 3, and each occurrence of $R_1$ independently comprises a moiety selected from the group consisting of hydrogen, aryl, heteroaryl, cycloalkyl, polycyclic, heterocyclic, alkenyl, alkynyl, solid support unit, polymer, and biomolecule;

$R_2$–$R_{13}$ each independently comprise a moiety selected from the group consisting of hydrogen, alkyl, alkenyl, alkynyl, aryl, heteroaryl, cycloalkyl, polycyclic, heterocyclic, alkoxy, acyl, amino, hydroxy, thio, halogen, cyano, nitro, trifluoromethyl, azido, imino, amido, phosphoryl, sulfonyl, silyl group, ether, alkylthio, carbonyl, solid support unit, polymer, and biomolecule;

$R_{14}$ comprises a functionality selected from the group consisting of ester moiety, O—$R_{15}$, wherein $R_{15}$ is selected from the group consisting of alkyl, cycloalkyl, aryl, heteroaryl, alkenyl, and alkynyl; ketone; oxime; carboxylic acid; aldehyde; phosphoryl; silyl; solid support unit; polymer and biomolecule, or a pharmaceutically acceptable salt thereof.

In particularly preferred embodiments of compositions represented by (I), preferably one occurrence of $R_1$ comprises a moiety selected from the group consisting of aryl, heteroaryl, cycloalkyl, polycyclic, heterocyclic, alkenyl, and alkynyl, and preferably, when A is a double bond and n=2, at least one occurrence of $R_1$ is hydrogen, whereby either an E (entgegen) or Z (zusammen) isomer is formed; $R_2$–$R_{13}$ each independently comprise hydrogen or alkyl; and $R_{14}$ comprises an ester moiety.

In still other preferred embodiments of compositions represented by (I), when n=2 or 3, preferably one occurrence of $R_1$ comprises a moiety selected from the group consisting of haloaryl, alkoxy, alkylaryl, polycyclyl, alkenylaryl, and alkynylaryl and is most preferably selected from the group consisting of phenyl, 3,4-Dichloro-phenyl, 4-methoxy-phenyl, 4-fluoro-phenyl, 1-napthyl, 2-furyl, and 3-furyl, methoxy, and substituted or unsubstituted alkenylaryl; and either one or two occurrences of $R_1$ comprise hydrogen.

In particularly preferred embodiments of compositions represented by (I), A is a double bond, n=2, and one occurrence of $R_1$ is selected from the group consisting of phenyl, 3,4-Dichloro-phenyl, 4-methoxy-phenyl, 4-fluoro-phenyl, 1-napthyl, 2-furyl, 3-furyl, methoxy, and substituted or unsubstituted alkenylaryl, and the second occurrence of $R_1$ is hydrogen, whereby an E (entgegen) isomer is generated.

The present invention also preferably provides compositions having the formula (II):

(II)

wherein,
$R_1$ and $R_2$ each independently comprise a moiety selected from the group consisting of hydrogen, aryl, heteroaryl, cycloalkyl, polycyclic, heterocyclic, alkenyl, alkynyl, solid support unit, polymer, and biomolecule;

$R_3$–$R_{13}$ each independently comprise a moiety selected from the group consisting of hydrogen, alkyl, alkenyl, alkynyl, aryl, heteroaryl, cycloalkyl, polycyclic, heterocyclic, alkoxy, acyl, amino, hydroxy, thio, halogen, cyano, nitro, trifluoromethyl, azido, imino, amido, phosphoryl, sulfonyl, silyl group, ether, alkylthio, carbonyl, solid support unit, polymer, and biomolecule;

$R_{14}$ comprises a functionality selected from the group consisting of ester moiety, O—$R_{15}$, wherein $R_{15}$ is selected from the group consisting of alkyl, cycloalkyl, aryl, heteroaryl, alkenyl, and alkynyl; ketone; oxime; carboxylic acid; aldehyde; phosphoryl; silyl; solid support unit; polymer and biomolecule, or a pharmaceutically acceptable salt thereof.

In particularly preferred embodiments of compositions represented by (II), either $R_1$ or $R_2$, but not both, comprises a moiety selected from the group consisting of aryl, heteroaryl, cycloalkyl, polycyclic, heterocyclic, alkenyl, and alkynyl, and either $R_1$ or $R_2$ comprises hydrogen, whereby either an E (entgegen) or Z (zusammen) isomer is formed; $R_3$–$R_{13}$ comprise hydrogen or alkyl; and $R_{14}$ comprises an ester moiety.

In still other preferred embodiments of compositions represented by (II), either $R_1$ or $R_2$, but not both, comprises a moiety selected from the group consisting of haloaryl, alkoxy, alkylaryl, polycyclyl, alkenylaryl, and alkynylaryl and is most preferably selected from the group consisting of phenyl, 3,4-Dichloro-phenyl, 4-methoxy-phenyl, 4-fluoro-phenyl, 1-napthyl, 2-furyl, and 3-furyl, methoxy, and substituted or unsubstituted alkenylaryl, and either $R_1$ or $R_2$, but not both, comprises hydrogen.

In particularly preferred embodiments of compositions represented by (II), $R_1$ is selected from the group consisting of phenyl, 3,4-Dichloro-phenyl, 4-methoxy-phenyl, 4-fluoro-phenyl, 1-napthyl, 2-furyl, 3-furyl, methoxy, and substituted or unsubstituted alkenylaryl, and $R_2$ is hydrogen, whereby an E (entgegen) isomer is generated.

In certain embodiments, the compositions of the present invention are represented by the general formula (I) and (II) and act as selective inhibitors of serotonin reuptake.

In other embodiments, the compositions of the present invention are represented by the general formula (I) and (II) and act as selective inhibitors of norepinephrine and serotonin reuptake.

As will be appreciated by one of ordinary skill in the art, these compounds are amenable to further functionalization at specific reactive groups, and one of ordinary skill in the art of organic synthesis will be able to make desired modifications to the inventive compounds.

As will also be appreciated by one of ordinary skill in the art, these compounds are amenable to combinatorial synthetic techniques and thus, as described herein in more detail, libraries of inventive compounds can be generated to optimize pharmocological parameters, including, but not limited to efficacy and safety. Additionally, these libraries can be assayed to determine those members which preferably bind to monoamine transporters and act as inhibitors of monoamine reuptake.

III. Pharmaceutical Compositions: As described herein, the inventive compounds are capable of binding to monoamine transporters and acting as inhibitors of monoamine reuptake. More preferably, these compounds are capable of acting as potent and selective inhibitors of serotonin and norepinephrine reuptake.

Thus, in another aspect, the present invention provides pharmaceutically acceptable compositions which comprise a therapeutically-effective amount of one or more of the compounds as described above (formula I and formula II), formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a transdermal patch or a sterile solution or suspension; (3) topical application, for example, as a cream, ointment or spray applied to the skin; or (4) intravaginally or intrarectally, for example, as a pessary, cream or foam.

Certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent. Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral 10 administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier. The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

As described above, actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition). The compounds according to the invention may be formulated for administration in any convenient way for use in human or veterinary medicine, by analogy with other pharmaceuticals.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

It will be appreciated that the pharmacological activity of the compounds of the invention can be demonstrated using standard pharmacological models which are known in the art, or can be demonstrated using the models that are described or cited herein below.

Furthermore, it will be appreciated that the inventive compounds and compositions can be incorporated or encapsulated in a suitable polymer matrix or membrane for site-specific delivery, or can be functionalized with specific targeting agents capable of effecting site specific delivery. These techniques, as well as other drug delivery techniques are well known in the art.

IV. Combinatorial Libraries

High throughput screening of natural products and fermentation broths has resulted in the discovery of several new drugs. At present, generation and screening of chemical diversity is being utilized extensively as a major technique for the discovery of lead compounds, and this is certainly a major fundamental advance in the area of drug discovery. Libraries of compounds, particularly small molecules, present potential for producing millions of new compounds for screening at a reasonable cost thus eliminating the time consuming, laborious and expensive procedures involved in the isolation, characterization, and synthesis of compounds obtained from natural sources (fermentation products) or conventional synthetic methods. Additionally, even after a "lead" compound has been identified, combinatorial techniques provide for a valuable tool for the optimization of desired biological activity.

As will be appreciated, the subject reactions readily lend themselves to the creation of combinatorial libraries of compounds for the screening of pharmaceutical, or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological property may be done by conventional methods. Thus, the present invention also provides methods for determining the ability of one or more inventive compounds to bind to monoamine transporters and block reuptake of monoamines comprising contacting a library of compounds as described herein with a monoamine transporter and determining the ability of one or more compounds in said library to bind to the monoamine transporter and block reuptake of monoamines.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents. Furthermore, diversification can occur while synthesizing the core inventive tropane analogs, or alternatively or additionally, can occur after the core inventive tropane analogs have been synthesized to generate diversity at specific functional groups.

A variety of techniques are available in the art for generating combinatorial libraries of small organic molecules. A few of these techniques are described below, but it will be understood that the present invention is not intended to be limited by the foregoing examples and descriptions. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c. f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags. The method of binary encoding will be described below:

1) Non-sequenceable Tagging: Binary Encoding

An alternative form of encoding the test compound library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker.

V. Other Uses:

It will be appreciated that the methods, compounds and libraries of the present invention can be utilized in various disciplines. For example, the compounds of the present invention may also be used as imaging agents when labeled with a radionuclide. For example, a radionuclide (such as tritium, iodine-125, iodine-131, iodine-123, astatine-210, carbon-11, carbon-14, nitrogen-13, fluorine-18) may be incorporated into, or attached directly to the core structure, as by halogenation; or the radionuclide (such as Tc-99m, Re-186) may be attached to a linking group or bound by a chelating group which is then attached to the compound by formula (I) or (II) directly, or by means of a linker. Radiolabeling techniques such as these are routinely used in the radiopharmaceutical industry.

Radiolabeled compounds of the invention are generally useful as imaging agents to diagnose neurological disease (e.g., a neurodegenerative disease) or a mental condition or to follow the progression or treatment of such a disease or condition in a mammal (e.g., a human). The radiolabeled compounds of the invention can be conveniently used in conjunction with imaging techniques such as positron emission tomogrpahy (PET) or single photon emission computerized tomography (SPECT).

Equivalents

Those skilled in the art will recognize, or be able to ascertain using no more than routine experimentation, numerous equivalents to the inventive compositions and methods of use thereof described herein. Such equivalents are considered to be within the scope of this invention and are covered by the following claims. Additionally, examples of particularly preferred embodiments are presented in the examples below and are intended to more particularly describe the present invention, but are not intended to limit the scope of the presently claimed invention.

Exemplification

Figure 2:
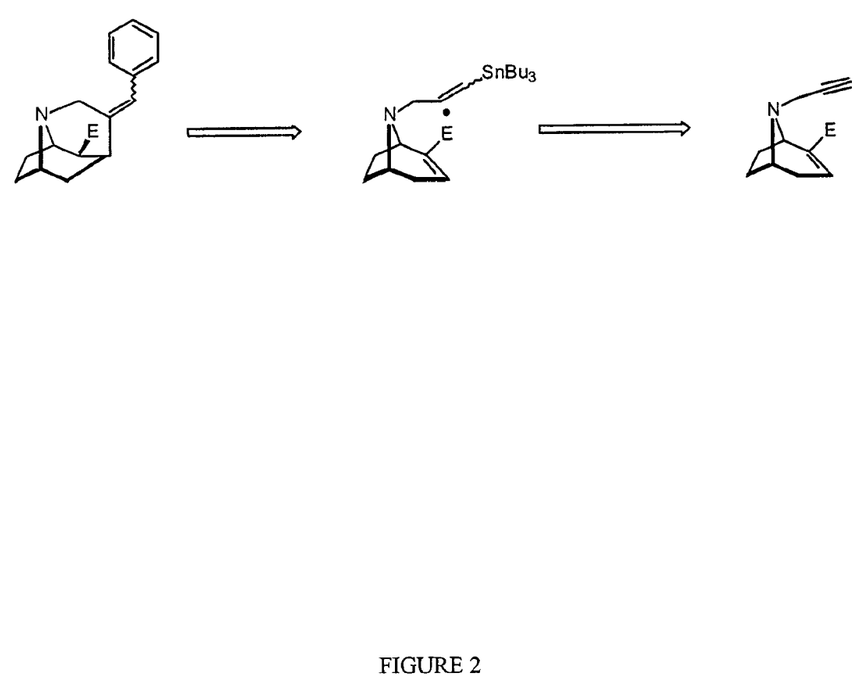
FIG. 2 depicts a retrosynthetic analysis of "N3 bridged" tropanes.

A) Synthesis of N3 bridged tropanes:

Retrosynthetic inspection of the envisioned "N3 bridged" tropanes reveals that the installation of the new bridge could be accomplished using an intramolecular radical cyclization strategy of a propargyl substituted anhydroecgonine methyl ester. This would lead to a tricyclic vinylstannane which in turn would be an ideal substrate to introduce the phenyl substituent by means of a Stille coupling (FIG. 2).

Figure 3:
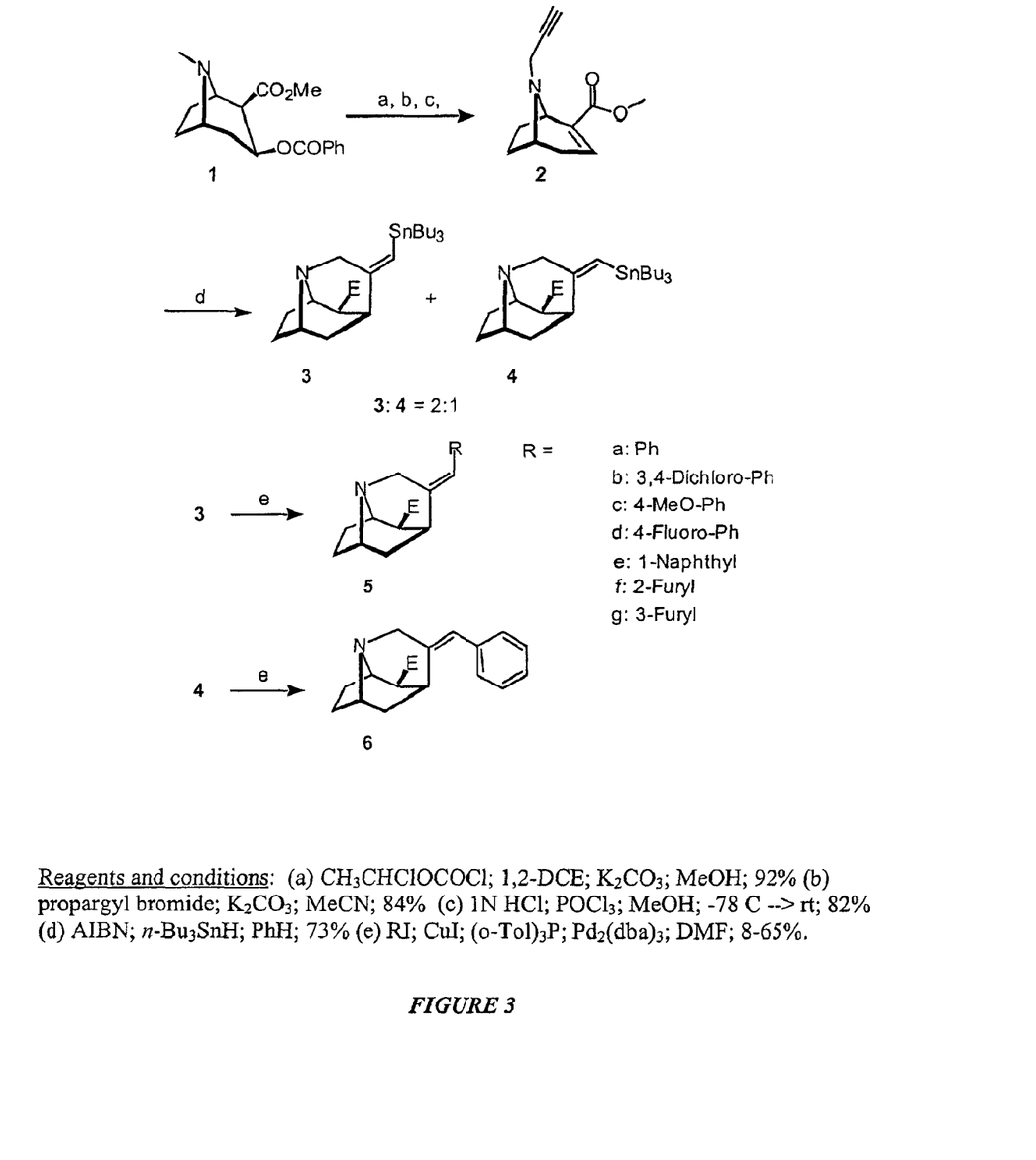
FIG. 3 depicts a general strategy for the preparation of bridge tropanes.

The preparation of the bridge tropanes was accomplished using the general strategy outlined in FIG. 3. Starting from cocaine (1), norcocaine was prepared by N-demethylation with -chloroethylchloroformate. Alkylation with propargytbromide afforded N-propargyl norcocaine in 84% yield. Saponification, dehydration and reesterification provided N-propargyl noranhydroecgonine methyl ester (2). The key step in the synthesis is a 6-endo-trig cyclization. It was envisioned that the vinyl radical, generated by addition of a stannyl radical to the triple bond, reacts in endo manner with the double bond favored by the electron withdrawing ester group, thus preventing a competing 5-exo-trig cyclization. The cyclization was carried out using syringe pump methodology, an excess of tributyltinhydride, and equimolar amounts of AIBN. The cyclization proceeded in good yields (73%) and with high diastereoselectivity as relates to the orientation of the ester group. Due to the bulky nature of the tributylstannyl residue the cyclized radical is trapped predominantly from the endo face of the tropane ring, thus giving rise to the formation of the tricycle (3 and 4) with the ester group in a orientation. We were unable to isolate any of the-ester. However, two double bond isomers (3 and 4) were obtained as a consequence of the radical nature of the tin hydride addition reaction. These two double bond isomers were easily separated by flash chromatography and the E/Z ratio is about 2:1. No attempts were made to assign the structure of the two isomers at this stage. Next, we converted the vinylstannane into the phenyl derivatives 5a and 6 by means of a Stille coupling. The use of DMF as solvent, tris(dibenzylideneacetone)dipalladium(0) as palladium source, tris(o-tolyl)phosphine as stabilizing ligand, and copper(I) iodide as additive as well as a strict temperature regimen, afforded the coupling products in good yields. Both isomeric vinylstannanes were reacted with iodobenzene, and the resulting products were analyzed by spectrometric methods using COSY, NOESY and TETCOR. From these NMR studies 5a was assigned the E-configuration and 6 the Z-configuration. The structure assignments were unambiguously confirmed by X-ray analysis. Since the Stille reaction proceeds with retention of configuration of the stannane, the configuration of the starting vinylstannanes was deduced from their phenyl derivatives.

B. Binding affinity and inhibition of reuptake:

These novel ligands have been tested for their binding affinity at the DAT as well as for the inhibition of reuptake of NE, 5-HT, and DA at their specific transporters. These data are shown in Table 1.

TABLE 1

Binding and uptake at monoamine transporters, $K_i \pm SE$ (nM)

| | [$^3$H]NE uptake | [$^3$H]5-HT uptake | [$^3$H]DA uptake | NE DA | NE 5-HT | 5-HT DA |
|---|---|---|---|---|---|---|
| 5a | 53.0 ± 16.1 | 1140 ± 70 | 480.6 ± 10.8 | 0.11 | 0.05 | 2.36 |
| 5b | 1000 ± 280 | 19.8 ± 0.5 | 1920 ± 260 | 0.52 | 50.6 | 0.01 |
| 5c | 187.1 ± 4.6 | 55.7 ± 3.8 | 3130 ± 160 | 0.06 | 3.37 | 0.02 |
| 5d | 584.4 ± 162.8 | 335.4 ± 45.5 | 6620 ± 460 | 0.09 | 1.74 | 0.05 |
| 5e | 5370 ± 580 | 120.7 ± 3.4 | 9720 ± 700 | 0.55 | 44.5 | 0.01 |
| 5f | 110.9 ± 12.7 | 3680 ± 190 | 2020 ± 190 | 0.05 | 0.03 | 1.82 |
| 5g | 163.5 ± 2.8 | 498.5 ± 65.5 | 1880 ± 10 | 0.09 | 0.33 | 0.26 |
| 6 | 1530 ± 150 | 7480 ± 250 | 5070 ± 310 | 0.3 | 0.2 | 1.48 |

As shown in Table 1, compound 5a lacking substitution on the phenyl ring shows potent inhibition of norepinephrine reuptake. It is also reasonably selective, as its $K_i$ at the 5-HTT and DAT are 20-fold and 9-fold higher, respectively. Compound 6 with the Z-configured double bond is only weakly active at all three transporters. While not wishing to be bound by any particular theory, the orientation of the phenyl ring is believed to be an important structural determinant of transporter activity in this ligand series.

The data found for 5a are correlated well with the data obtained for the p-methoxy substituted compound 5c as well as the two furyl analogs 5f and 5g. Their inhibition of norepinephrine reuptake is somewhat lower but still excellent. It is of further interest to note that 3,4-dichlorophenyl substitution in the WIN series leads to some of the most DAT active compounds to be reported ($IC_{50}$=0.79 nM). On the other hand, a certain electron density in the phenyl ring seems to be important for binding, as a fluoro substituent decreases reuptake activity by a factor of about 10 (5d vs. 5a). Nearly the opposite is the case for the 5-HTT. Compound 5b in fact exhibits a remarkable potency and selectivity for the 5-HTT, showing about 100-fold higher activity at 5-HTT vs. DAT and about 50-fold higher activity at 5-HTT vs. the NET. 5e is also fairly NET selective, but less potent compared to 5b.

Compound 5c has a NET activity between that of 5b and 5e. However, its activity at the 5-HTT is striking, especially given its relatively poor activity at the DAT (50-fold selectivity for 5-HTT vs. DAT). This ligand thus acts as a selective norepinephrine and serotonin reuptake inhibitor (SSNRI). The drug venlafaxine, a clinically important antidepressant, is one of the first SSNRIs to enter the marketplace. As venlafaxine shows poorer uptake activity ($K_i$ (NE uptake)=1644 nM, (5-HT-uptake)=102 nM), in comparison to 5c, this newly designed ligand may serve as a lead compound for the creation of a new class of SSNRIs as antidepressants.

As already discussed, compound 5a appears to be a reasonably selective norepinephrine reuptake inhibitor (SNRI) that is expected to exhibit only limited cholinergic properties. While the classic tricyclic antidepressants exhibit reuptake inhibition of norepinephrine, they, as a class, exhibit cholinergic properties that contribute to their adverse side effect profile. The synthesis of ligands of this class has long proved elusive, and only recently, with the introduction of reboxetine into the European market, has the first NRI became available. Reboxetine exhibits a safe side-effect profile and seems to be well tolerated. The activity of Reboxetine at the NET is only moderate (150 nM). Due to the improved activity of 5a at the NET, it may prove to be more efficacious for the treatment of depression.

REFERENCES

1. Boyd, J. H.; Weissman, M. M. *Arch. Gen. Psychiatry* 1981, 38, 1039–1046.
2. Cookson, J. Side-effects of antidepressants. *Br. J. Psychiatry* 1993, 163, 20–24.
3. Broekkamp, C. L. E.; Leysen, D.; Peters, B. W. M. M.; Pinder, R. M. *J. Med. Chem.* 1995, 38, 4615–4633.
4. Briner, K.; Dodel, R. C. *Current Pharm. Design* 1998, 4, 291–302.
5. Horst, W. D.; Preskorn, S. H. *J. Affect. Disord.* 1998, 51, 237–254.
6. Anderson, I. M.; Tomenson, B. M. J. Pharm. 1994, 8, 238–249.
7. Byrne, S. E.; Rothschild A. *J. Clin. Psychatry* 1998, 59, 279–288.
8. Schildkraut, J. *J. Am. J. Psychiatry* 1965, 122, 509–522.
9. Lapin, I. P.; Oxenkrug, G. F. *Lancet* 1969, 1, 132–136.
10. Smith, M. P.; Hoepping, A.; Johnson, K. M.; Trzcinska, M.; Kozikowski, A. P. *Drug Disc. Today* 1999, 4, 322–332.
11. Nelson, N. *J. Neurochem.* 1998 71, 1785–1803.
12. Kilty, J. E.; Lorang, D.; Amara, S. G. *Science* 1991 254, 578–579
13. Smith, M. P.; Johnson, K. M.; Zhang, M.; Flippen-Anderson, J. L.; Kozikowski, A. P. *J. Am. Chem. Soc.* 1998, 120, 9072–9073.
14. Olofson, R. A.; Martz, J. T.; Senet, J. P.; Piteau, M.; Malfroof, T. *J. Org. Chem.* 1984, 49, 2081–2082.
15. Giese, B.; Kopping, B.; Goebel, T.; Dickhaut, J.; Thoma, G.; Kulicke, K. J.; Trach, F. *Org. React.* 1996, 48, 301–856.
16. Nozaki, K.; Oshima, K.; Utimoto, K. *J. Am. Chem. Soc.* 1987, 109, 2547–2549.
17. Corey, E. J.; Ulrich, P.; Fitzpatrick, J. M. *J. Am. Chem. Soc.* 1976, 98, 222.
18. Stille, J. K.; Groh, B. L. *J. Am. Chem. Soc.* 1987, 109, 813–817.
19. Carroll, F. Y.; Mascarella, S. W.; Kuzernko, M. A.; Gao, Y.; Abraham, P.; Lewin, A. H.; Boja, J. W.; Kuhar, M. J. *J. Med. Chem.* 1994, 37, 2865–2873.
20. Owens, M. J.; Morgan, W. N.; Plott, S. J.; Nemeroff, C. B. *J. Pharmacol. Exp. Ther.* 1997, 283, 1305–1322.
21. Riva, M.; Brunello, N.; Rovescalli, A. C.; Galimberti, R.; Crafagna, N.; Carminati, P.; Pozzi, O.; Ricciardi, S.; Roncucci, R.; Rossi, A.; Racagni, G. *J. Drug Dev.* 1989, 1, 243–253.

All of the above-cited references and publications are hereby incorporated by reference.

We claim:

1. A compound represented by formula (II):

(II)

wherein,
  $R_1$ and $R_2$ each independently are selected from the group consisting of hydrogen, aryl, and heteroaryl,
  $R_3$–$R_{13}$ are hydrogen;
  $R_{14}$ is selected from the group consisting of —$R_{16}$C(O)O$R_{15}$, —OC(O)$R_{15}$, —O—$R_{17}$, wherein $R_{17}$ is selected from the group consisting of alkyl, cycloalkyl, aryl, heteroaryl, alkenyl, and alkynyl; —$R_{16}$(O)C$R_{15}$; —C($R_{15}$)=N(OH); carboxylic acid; —$R_{16}$C(O)H; -$Q_2$-P($Q_1$)(O$R_{15}$)$_2$; and silyl;
  $R_{15}$ represents independently for each occurrence hydrogen, alkyl, alkenyl, alkynyl, or aryl;
  $R_{16}$ represents independently for each occurrence a bond or an alkyl, alkenyl, alkynyl, or aryl biradical;
  $Q_1$ represents independently for each occurrence S or O; and
  $Q_2$ represents independently for each occurrence O, S, or N$R_{15}$;
or a pharmaceutically acceptable salt thereof.

2. The compound of claim 1, wherein $R_1$ is selected from the group consisting of aryl, and heteroaryl, and $R_2$ is hydrogen, or $R_2$ is selected from the group consisting of aryl, and heteroaryl, and $R_1$ is hydrogen, and $R_{14}$ is —$R_{16}$C(O)O$R_{15}$ or —OC(O)$R_{15}$.

3. The compound of claim 1, wherein $R_1$ is selected from the group consisting of haloaryl, and alkylaryl and $R_2$ is hydrogen; or $R_2$ is selected from the group consisting of haloaryl, and alkylaryl; and $R_1$ is hydrogen.

4. The compound of claim 1, wherein $R_1$ is selected from the group consisting of phenyl, 3,4-Dichloro-phenyl, 4-methoxy-phenyl, 4-fluoro-phenyl, 1-napthyl, 2-furyl, 3-furyl, and substituted or unsubstituted alkenylaryl; and $R_2$ is hydrogen.

5. The compound of claim 1, wherein $R_1$ is 4-methoxy-phenyl, $R_2$ is hydrogen, and $R_{14}$ is —$R_{16}$C(O)O$R_{15}$ or —OC(O)$R_{15}$.

6. The compound of claim 1, wherein $R_1$ is phenyl, $R_2$ is hydrogen, and $R_{14}$ is —$R_{16}$C(O)O$R_{15}$ or —OC(O)$R_{15}$.

7. A pharmaceutical composition comprising a compound of formula (II):

(II)

wherein, $R_1$ and $R_2$ each independently are selected from the group consisting of hydrogen, aryl, and heteroaryl;

$R_3$–$R_{13}$ are hydrogen, $R_{14}$ is selected from the group consisting of —$R_{16}$C(O)O$R_{15}$, —OC(O)$R_{15}$, —O—$R_{17}$, wherein $R_{17}$ is selected from the group consisting of alkyl, cycloalkyl, aryl, heteroaryl, alkenyl, and alkynyl; —$R_{16}$(O)C$R_{15}$; —C($R_{15}$)=N(OH); carboxylic acid; —$R_{16}$C(O)H; -$Q_2$-P($Q_1$)(O$R_{15}$)$_2$; and silyl;

$R_{15}$ represents independently for each occurrence hydrogen, alkyl, alkenyl, alkynyl, or aryl;

$R_{16}$ represents independently for each occurrence a bond or an alkyl, alkenyl, alkynyl, or aryl biradical;

$Q_1$ represents independently for each occurrence S or O; and $Q_2$ represents independently for each occurrence O, S, or N$R_{15}$;

or a pharmaceutically acceptable salt thereof; and a pharmaceutically acceptable carrier.

8. The pharmaceutical composition of claim 7, wherein $R_1$ is selected from the group consisting of aryl, and heteroaryl, and $R_2$ is hydrogen, or $R_2$ is selected from the group consisting of aryl, and heteroaryl, and $R_1$ is hydrogen, and $R_{14}$ is —$R_{16}$C(O)O$R_{15}$ or —OC(O)$R_{15}$.

9. The pharmaceutical composition of claim 7, wherein $R_1$ is selected from the group consisting of haloaryl, and alkylaryl; and $R_2$ is hydrogen; or $R_2$ is selected from the group consisting of haloaryl, and alkylaryl; and $R_1$ is hydrogen.

10. The pharmaceutical composition of claim 7, The compound of claim 1, wherein $R_1$ is selected from the group consisting of phenyl, 3,4-Dichloro-phenyl, 4-methoxy-phenyl, 4-fluoro-phenyl, 1-napthyl, 2-furyl, 3-furyl; and $R_2$ is hydrogen.

11. A method for treating depression or cocaine addiction comprising administering to a human in need thereof a therapeutically effective dose of a compound of formula (II):

(II)

wherein, $R_1$ and $R_2$ each independently are selected from the group consisting of hydrogen, aryl, and heteroaryl;

$R_3$–$R_{13}$ are hydrogen, $R_{14}$ is selected from the group consisting of —$R_{16}$C(O)O$R_{15}$, —OC(O)$R_{15}$, —O—$R_{17}$, wherein $R_{17}$ is selected from the group consisting of alkyl, cycloalkyl, aryl, heteroaryl, alkenyl, and alkynyl; —$R_{16}$(O)C$R_{15}$; —C($R_{15}$)=N(OH); carboxylic acid; —$R_{16}$C(O)H; -$Q_2$-P($Q_1$)(O$R_{15}$)$_2$; and silyl;

$R_{15}$ represents independently for each occurrence hydrogen, alkyl, alkenyl, alkynyl, or aryl;

$R_{16}$ represents independently for each occurrence a bond or an alkyl, alkenyl, alkynyl, or aryl biradical;

$Q_1$ represents independently for each occurrence S or O; and $Q_2$ represents independently for each occurrence O, S, or N$R_{15}$;

or a pharmaceutically acceptable salt thereof.

12. The method of claim 11, wherein $R_1$ is selected from the group consisting of aryl, and heteroaryl, and $R_2$ is hydrogen, or $R_2$ is selected from the group consisting of aryl, and heteroaryl, and $R_1$ is hydrogen; and $R_{14}$ is —$R_{16}$C(O)O$R_{15}$ or —OC(O)$R_{15}$.

13. The method of claim 11, wherein $R_1$ is selected from the group consisting of haloaryl, and alkylaryl; and $R_2$ is hydrogen; or $R_2$ is selected from the group consisting of haloaryl, and alkylaryl; and $R_1$ is hydrogen.

14. The method of claim 11, wherein $R_1$ is selected from the group consisting of phenyl, 3,4-Dichloro-phenyl, 4-methoxy-phenyl, 4-fluoro-phenyl, 1-napthyl, 2-furyl, 3-furyl; and $R_2$ is hydrogen, and the compound is an E (entgegen) isomer.

15. The method of claim 11, wherein cocaine addiction is treated.

16. The method of claim 11, wherein depression is treated.

* * * * *